US009079923B2

(12) United States Patent
Lei et al.

(10) Patent No.: US 9,079,923 B2
(45) Date of Patent: Jul. 14, 2015

(54) MULTIDENTATE KETOIMINE LIGANDS FOR METAL COMPLEXES

(75) Inventors: Xinjian Lei, Vista, CA (US); Daniel P. Spence, Carlsbad, CA (US)

(73) Assignee: Air Products and Chemicals, Inc., Allentown, PA (US)

( * ) Notice: Subject to any disclaimer, the term of this patent is extended or adjusted under 35 U.S.C. 154(b) by 816 days.

(21) Appl. No.: 13/187,833

(22) Filed: Jul. 21, 2011

(65) Prior Publication Data

US 2012/0201958 A1  Aug. 9, 2012

Related U.S. Application Data

(60) Provisional application No. 61/370,924, filed on Aug. 5, 2010.

(51) Int. Cl.
C07F 3/00 (2006.01)
C23C 16/00 (2006.01)
C23C 16/455 (2006.01)

(52) U.S. Cl.
CPC ........... *C07F 3/003* (2013.01); *C23C 16/45553* (2013.01)

(58) Field of Classification Search
None
See application file for complete search history.

(56) References Cited

U.S. PATENT DOCUMENTS

| | | | |
|---|---|---|---|
| 5,782,986 | A | 7/1998 | Butterbaugh et al. |
| 5,820,664 | A | 10/1998 | Gardiner et al. |
| 6,620,971 | B2 | 9/2003 | Chang et al. |
| 6,752,869 | B2 | 6/2004 | Lee et al. |
| 7,132,556 | B2 | 11/2006 | Benvenuti et al. |
| 7,691,984 | B2 | 4/2010 | Lei et al. |
| 7,723,493 | B2 | 5/2010 | Lei et al. |
| 2005/0170092 | A1 | 8/2005 | Benvenuti et al. |
| 2006/0258173 | A1 | 11/2006 | Xiao et al. |
| 2007/0248754 | A1 | 10/2007 | Lei et al. |
| 2008/0032062 | A1 | 2/2008 | Meiere |
| 2009/0136684 | A1 | 5/2009 | Peters et al. |
| 2009/0302434 | A1 | 12/2009 | Pallem et al. |
| 2010/0078601 | A1 | 4/2010 | Pallem et al. |

FOREIGN PATENT DOCUMENTS

| | | | |
|---|---|---|---|
| EP | 369297 | B1 | 8/1993 |
| EP | 1227079 | A2 | 7/2002 |
| EP | 1 273 683 | A2 | 1/2003 |
| EP | 1 676 849 | A | 7/2006 |
| EP | 1 676 849 | A1 | 7/2006 |
| EP | 1 676 850 | A | 7/2006 |
| EP | 1 676 850 | A1 | 7/2006 |
| EP | 1 849 789 | A1 | 10/2007 |
| JP | 02-188564 | A | 7/1990 |
| JP | 03-163055 | A | 7/1991 |
| JP | 3227891 | A1 | 10/1991 |
| JP | 06-298714 | A | 10/1994 |
| JP | 6-298714 | A | 10/1994 |
| JP | 6298714 | A2 | 10/1994 |
| JP | 08-259528 | A | 10/1996 |
| JP | 2000-503805 | A | 3/2000 |
| JP | 2002-193988 | A | 7/2002 |
| JP | 2002-302473 | A | 10/2002 |
| JP | 2002-338590 | A2 | 11/2002 |
| JP | 2004-014813 | A | 1/2004 |
| JP | 2005-531619 | A | 10/2005 |
| KR | 10-2009-0007099 | A | 4/2007 |
| KR | 10-2009-0007102 | A | 4/2007 |
| TW | 200403249 | B | 3/2004 |
| TW | I256078 | | 6/2006 |
| TW | I256078 | B | 6/2006 |
| WO | 02/18394 | A1 | 3/2002 |
| WO | 2004002946 | A1 | 1/2004 |

OTHER PUBLICATIONS

Matthews, J.S., et al; "CVD of MgO from a Mg(B-ketoiminate)2: Preparation, Characterization, and Utilization of an Intramolecularly Stabilized, Highly Volatile, Thermally Robust Precursor"; Chemical Vapor Deposition; vol. 6, No. 3; 2000; pp. 129-132.

Edelmann, F.T.; "Lanthanide Amidinates and Guanidinates: from Laboratory Curiosities to Efficient Homogeneous Catalysts and Precursors for Rare-Earth Oxide Thin Films"; The Royal Society of Cehmistry; vol. 38; 2009; pp. 2253-2268.

Husekova, K., et al.; "Preparation of High Permittivity GdScO3 Films by Liquid Injection MOCVD"; EXC Transactions; vol. 25, No. 8; 2009; pp. 1061-1064.

Jones, A.C., et al.; "Recent Developments in the MOCVD and ALD of Rare Earth Oxides and Silicates"; Materials Science and Engineering; vol. 118; 2005; pp. 97-104.

Katamreddy, R., et al.; "Atomic Layer Deposition of Rare-Earth Oxide Thin Films for High-k Dielectric Applications"; ECS Transactions; vol. 19, No. 2; 2009; pp. 525-536.

Mao, L., et al.; "Syntheses of {(MeC5H4)2Ln(THF)[O—CN(i-Pr)2—NPh]} (Ln ) Y, Er, Yb) and the X-ray Crystal Structure of the Yttrium Complex: The Active Species for Polymerization of Phenyl Isocyanate by (Diisopropylamido) bis(methylcyclopentadienyl-)lanthanides"; Organometallics; vol. 16; 1997; pp. 3711-3714.

Nief, F., et al.; "Heterocyclopentadienyl Complexes of Group-3 Metals"; Eur. J. Inorg. Chem.; 2001; pp. 891-904.

(Continued)

*Primary Examiner* — Alicia L Otton
(74) *Attorney, Agent, or Firm* — Rosaleen P. Morris-Oskanian

(57) ABSTRACT

The present invention is a plurality of metal-containing complexes of a multidentate ketoiminate.

14 Claims, 2 Drawing Sheets

(56) References Cited

OTHER PUBLICATIONS

Paivasaari, J., et al.; "Synthesis, structure and properties of volatile lanthanide complexes containing amidinate ligands: application for Er2O3 thin film growth by atomic layer deposition"; J. Mater. Chem.; vol. 15; 2005; pp. 4224-4233.

Douglas L Schulz, et al, New Precursors for Barium MOCVD, Inorg. Chem., 1993, 249-250, 32, 3, Amer. Chem. Soc.

Sergej Pasko, et al, Synthesis and Characterization of New Alkaline Earth Metal B-ketoiminates. Inorg. Chem., 2005, 483-487, 8. Elsevier B.V.

Pier Luigi Franceschini, et al, Volatile B-Ketoiminato- and B-Diketiminator-Based Zirconium Complexes as Potential MOCVD Precursors, Inorg. Chem., 2003, 7273-7282, 42, Amer. Chem. Soc.

Tsung-Yi Chou, et al, Synthesis and Characterization of Tris (B-ketoiminator) ruthenium(III) Complexes: . . . Chem. Vap. Deposition, 2004, 10, 3, 149-158.

Sunkwon Lim, et al, A Study on the Development of Chemical Vapor Deposition Precursors. 4. Synthesis and . . . Chem. Mater., 2002, 14, 1548-1554, Amer. Chem. Soc.

Sunkwon Lim, et al, A Study on the Development of CVD Precursors V—synthesis and Characterization of new N-alkoxy-B-ketoiminate Comlexes of Titanium, Jour. Organ. Chem., 2004, 689, 224-237, Elsevier B.V.

Nikki L. Edleman, et al, Synthesis and Characterization of Volatile, Fluorine-Free B-Ketoiminate Lanthanide MOCVD Precursors and Their Implementation In . . . Inorg. Chem., 2002, 41, 5005-5023, Amer. Chem. Soc.

Edwards D.A., et al; "Aerosol-Assisted Chemical Vapour Deposition (AACVD) of Silver Films from Triphyenylphospine Adducts of Silver .Beta.-diketonates and .Beta.-diketoiminates, Including the Structure of [Ag(hfac) (PPh3)]"; Journal of Materials Chemistry; vol. 9, No. 8; 1999; pp. 1771-1780; XP002372344.

Bouquillon S, et al; "Simultaneous Generation of Anionic and Neutral Palladium(II) Complexes from Eta3- Allylpalladium Chloride Dimer and Fluorinated Beta-Enaminones"; European Journal of Organic Chemistry; No. 24; 2003; pp. 4714-4720; XP002372342.

Tung Y-L, et al; "Synthesis and Characterization of Allyl(Beta-Ketoiminato)Palladium (II) Complexes: New Precursors for Chemical Vapor Deposition of Palladium Thin Films"; Organometallics; vol. 18, No. 5; Feb. 5, 1999; pp. 864-869; XP002372343.

Collier W, et al; "Kinetics of Acid Hydrolysis of Nickel(II) and Copper(II) Compounds with the Cyclic Diamines 1,5-Diazocane, and 4,4-Dimethyl-7-(5,5,7-Trim Eihyl-1,4-Diazepan-1-Yl)-5-Azaheptan-2-Ol"; Australian Journal of Chemistry; vol. 42, No. 9; 1989; pp. 1611-1616; XP009089097.

Konefal E, et al; "Coordination Modes of Polydentate Ligands. 1. Template Synthesis of Complexes of Nickel(2+), Copper(2+), and Cobalt(2+) with Pentadentate and Hexadentate Ligands: Structure of a Highly Distorted Six-Coordinate Cobalt(2+) Complex"; Inorganic Chemistry; vol. 23, No. 5;1984; pp. 538-545; XP009079427.

Curtis N.F., et al; "Preparations, Magnetic Susceptibility and Structural Studies of Trinuclear Copper(II) Compounds of 4,4,9,9-Tetramethyl-5,8-Diazadodecarre-2,11-Diol"; Australian Journal of Chemistry; vol. 41, No. 10; 1988; pp. 1545-1555; XP009089095.

Morgan, K.R., et al; "Preparation, and Complexes with Nickel(II) and Copper(II), of a Diazepane Amine Alcohol. The Structure of [4,4-Dimethyl-7-(5,5,7-Trimethy1-1,4-Diazeparl-1-Yl)-5-Azaheptan-2-Ol]Nickel (II) Perchlorate"; Austrailian Journal of Chemistry; vol. 36, No. 7; 1983; pp. 1341-1351; XP009089096.

Martin J.W.L., et al; "Fluorinated Alkoxides. Part XIII. The Reduction of Beta-Imino-Alkoxy Complexes to give Stable, Polydentate, Amino Alcohols"; Canadian Journal of Chemistry; vol. 56, No. 23; 1978; pp. 2966-2969; XP009089101.

Daniel B. Studebaker, et al, Encapsulating Bis(B-Ketoiminator) Polyethers, Volatile, Fluorine-Free Barium Precursors for Metal . . . Inorg. Chem. 2000, 39, 3148-3157, Amer. Chem. Soc.

Jason S. Matthews, et al, Group 2 Element Precursors for the Chemical Vapor Deposition of Electronic Materials, Adv. in Inorg. Chem., 50, 2000,173-192, Academic Press.

Loeb, S.J., et al; "Coordination Modes of Polydentate Ligands. 2. Template Synthesis of Four-, Five-, and Six-Coordinate Fluorinated Schiff-Base Complexes of Ni2+: Structure of an Octahedral Ni2+ Complex Containing Two Tridentate Ligands"; Inorganic Chemistry; vol. 23; 1984; pp. 1509-1512.

Becht, M., et al; "117. Synthesis Crystal Structure, and Thermal Behaviour of Some New Copper Complexes with Tridentate β-Iminoketone Ligands"; Helvetica Chimica Acta; 1994; vol. 77(5); pp. 1288-1298.

Yun, Chi, Ph.D.; "Design, Synthesis and Application of a New Chemical Vapor Deposition Precursor"; Chemistry Research Institute; Oct. 2004; Doctoral Dissertation; pp. 1-17.

Peng, H., et al.; "Synthesis, Reactivity, and Characterization of Sodium and Rare-Earth Metal Complexes Bearing a Dianionic N-Aryloxo-Functionalized B-Ketoiminate Ligand"; Inorg. Chem.; vol. 47; 2008; pp. 9828-9835.

Wilkinson, G., et al.; Steroids. LXIII.' Synthesis of A4-19-Norpregnene-11B,17x, 21-Triol-3,20 Dione (19-Norhydrocortisone) and Related 19-Noradrenal Hormones ; J. Am. Chem. Soc.; vol. 76, No. 23; 1954; p. 6210.

Matthews, et al.; Chemical Vapor Deposition; vol. 6, No. 3; 2000; pp. 129-132.

Chou, Tsung-Yi, Synthesis and Characterization of Tris(B-ketoiminato)ruthenium(III) Complexes: Potential Precursors for CVD of Ru and RuO2 Thin Films, Chemical Vapor Deposition, 2004, pp. 149-158, vol. 10 No. 3.

Edleman, Nikki L., Synthesis and Characterization of Volatile, Fluorine-Free B-Ketoiminate Lanthanide MOCVD Precursors and Their Implementation in Low-Temperature Growth of Epitaxial CeO2 Buffer Layers for Superconducting Electronics, Inorganic Chemistry, 2002, pp. 5005-5023, vol. 41.

Lim, Sunkwon, A Study on the Development of CVD Precursors V—syntheses and Characterization of New N-alkoxy-B-ketoiminate Complexes of Titanium, Journal of Organometallic Chemistry, 2004, pp. 224-237, vol. 689.

Lim, Sunkwon, A Study on the Development of Chemical Vapor Deposition Precursors. 4. Syntheses and Characterization of New N-Alkoxo-B-ketoiminate Complexes of Niobium and Tantalum, Chemical Material, 2002, pp. 1548-1554, vol. 14.

Matthews, Jason S., CVD of MgO from a Mg(B-ketoiminate)2: Preparation Characterization, and Utilization of an Intramolecularly Stabilized, Highly Volatile, Thermally Robust Precursor, Chemical Vapor Deposition, 2000, pp. 129-132, vol. 6, No. 3.

Ouattara T. S., Synthesis and Characterization of bis[4-N-(cyclohexylimino)-2-pentanonato]magnesium(II), Journal of Coordination Chemistry, 2005, pp. 461-465, vol. 58, No. 5.

Pasko, Sergej., Synthesis and Characterization of New Alkaline Earth Metal B-ketoiminates. The First Structurally Characterized Strontium B-ketoiminate, Inorganic Chemistry Communications, 2005, pp. 483-487, vol. 8.

Schulz, Douglas L., New Precursors for Barium MOCVD. B-Ketoiminate Complexes Containing Appended Polyether "Lariats", Inorganic Chemistry, 1993, pp. 249-250, vol. 32.

MULTIDENTATE KETOIMINE LIGANDS FOR METAL COMPLEXES

CROSS REFERENCE TO RELATED APPLICATION

The present patent application claims the benefit of prior U.S. Provisional Patent Application Ser. No. 61/370,924 filed 5 Aug. 2010.

BACKGROUND OF THE INVENTION

The present invention is in the field of metal ligands for delivery of metals to a reaction zone for deposition of metal-containing films in the field of semiconductor substrate fabrication.

Industry is continually looking for precursors to deliver desired metals to a reaction zone and a target substrate where the precursors are preferably liquid for ease of delivery, reversibly bind desired metals and result in clean deposition of the metal-containing on the target substrate under low reaction temperatures and modest reaction conditions within the thermal budget of the semiconductor device being fabricated. Thermal stability of the ligand portion of the metal ligand precursor is desirable so that premature decomposition does not occur, particularly in an atomic layer deposition process. Clean intake leaving groups of the ligand separating from the metal upon metal deposition is also an advantage.

Prior art relevant to this field includes the following.
U.S. Pat. No. 7,132,556.
U.S. Pat. No. 6,620,971.
Chou, T.-Y., Y.-H. Lai, Y.-L. Chen, Y. Chi, K. R. Prasad, A. J. Carty, S.-M. Peng and G.-H. Lee (2004). "Synthesis and characterization of tris(β-ketoiminato)ruthenium(III) complexes: Potential precursors for CVD of Ru and $RuO_2$ thin films." Chemical Vapor Deposition 10(3): 149-158.
Edleman, N. L., A. Wang, J. A. Belot, A. W. Metz, J. R. Babcock, A. M. Kawaoka, J. Ni, M. V. Metz, C. J. Flaschenriem, C. L. Stern, L. M. Liable-Sands, A. L. Rheingold, P. R. Markworth, R. P. H. Chang, M. P. Chudzik, C. R. Kannewurf and T. J. Marks (2002). "Synthesis and characterization of volatile, fluorine-free β-ketoiminate lanthanide mocvd precursors and their implementation in low-temperature growth of epitaxial $ceo_2$ buffer layers for superconducting electronics." Inorganic Chemistry 41(20): 5005-5023.
U.S. Pat. No. 5,820,664.
U.S. Pat. No. 6,752,869.
U.S. Pat. No. 7,723,493.
U.S. Pat. No. 7,691,984.
US2007/0248754.
Lim, S., B. Choi, Y.-S. Min, D. Y. Kim, I I, S. S. Lee and I.-M. Lee (2004). "A study on the development of CVD precursors. V. Syntheses and characterization of new N-alkoxy-b-ketoiminate complexes of titanium." Journal of Organometallic Chemistry 689(1): 224-237.
Lim, S., J. C. Lee, D. S. Sohn, W. I. Lee and I.-M. Lee (2002). "A Study on the Development of Chemical Vapor Deposition Precursors. 4. Syntheses and characterization of new n-alkoxo-β-ketoiminate complexes of niobium and tantalum." Chemistry of Materials 14(4): 1548-1554.
Matthews, J. S, and J. O. Just B. Obi-Johnson W. S. Rees (2000). "CVD of MgO from a Mg(ketoiminate)$_2$: Preparation, characterization, and utilization of an intramolecularly stabilized, highly volatile, thermally robust precursor." Chemical Vapor Deposition 6(3): 129-132.
Ouattara, T. S., R. J. Butcher and J. S. Matthews (2005). "Synthesis and characterization of bis[4-N-(cyclohexylimino)-2-pentanonato]magnesium(II)." Journal of Coordination Chemistry 58(5): 461-465.
Pasko, S., L. G. Hubert-Pfalzgraf, P. Richard and A. Abrutis (2005). "Synthesis and characterization of new alkaline earth metal β-ketoiminates. The first structurally characterized strontium β-ketoiminate." Inorganic Chemistry Communications 8(5): 483-487.
JP3227891B2.
Schulz, D. L., B. J. Hinds, C. L. Stern and T. J. Marks (1993). "New Precursors for Barium Mocvd—Beta-Ketoiminate Complexes Containing Appended Polyether Lariats." Inorganic Chemistry 32(3): 249-250.
US2006/0258173.
U.S. Provisional Patent Application Ser. No. 61/254,253 filed Oct. 23, 2009.

BRIEF SUMMARY OF THE INVENTION

The present invention is a compound having the formula:

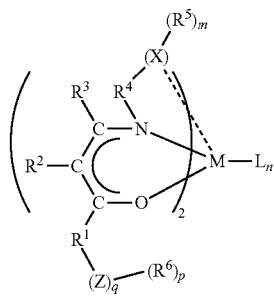

wherein M is selected from the group consisting of magnesium, calcium, strontium, barium; wherein $R^1$ is selected from the group consisting of branched alkyl, fluoroalkyl, cycloaliphatic, and aryl, having from 4 to 10 carbon atoms; $R^2$ is selected from the group consisting of hydrogen, alkyl, alkoxy, cycloaliphatic, and aryl; $R^3$ is linear or branched selected from the group consisting of alkyl, fluoroalkyl, cycloaliphatic, and aryl; $R^4$ is a liner or branched alkyl bridge having 2 to 10 carbon atoms; $R^{5-6}$ are individually selected from the group consisting of $C_{1-2}$ alkyl; L is a neutral ligand coordinated to the metal via an oxygen or nitrogen atom; n is 0 or 1; X and Z are independently selected from O or N; when X is N, m is 2 and the two $R^5$ are each independently selected from the group consisting of $C_{1-2}$ alkyl; when X is O, m is 1 and $R^5$ is selected from the group consisting of $C_{1-2}$ alkyl; q can be 0 or 1; when q is 0, Z and $R^6$ are not present; when q is 1, Z is either N, p is 2 and the two $R^6$ are each independently selected from the group consisting of $C_{1-2}$ alkyl; or Z is O, p is 1 and $R^6$ is selected from the group consisting of $C_{1-2}$ alkyl; when q is 0, n must be 1; when X is N and Z is O and q is 1, n must be 1.

DETAILED DESCRIPTION OF THE INVENTION

Figure 1:
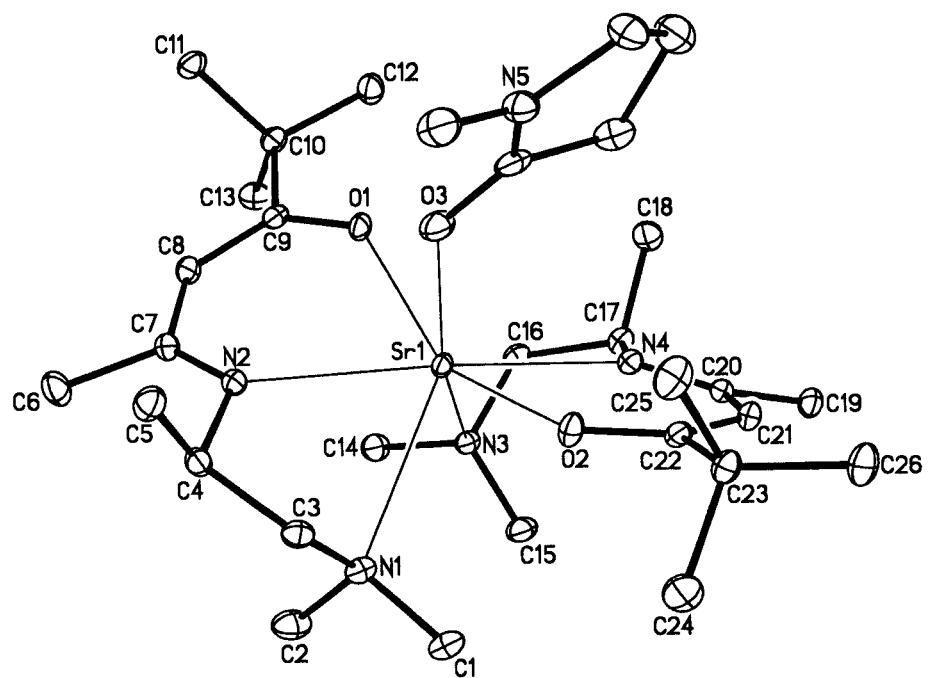
FIG. 1 is a crystal structure of bis(2,2-dimethyl-5(1-dimethylamino-2-propylimino)-3-hexanonato-N,O,N')strontium 1-Methyl-2-pyrrolidinone adduct.
Figure 2:
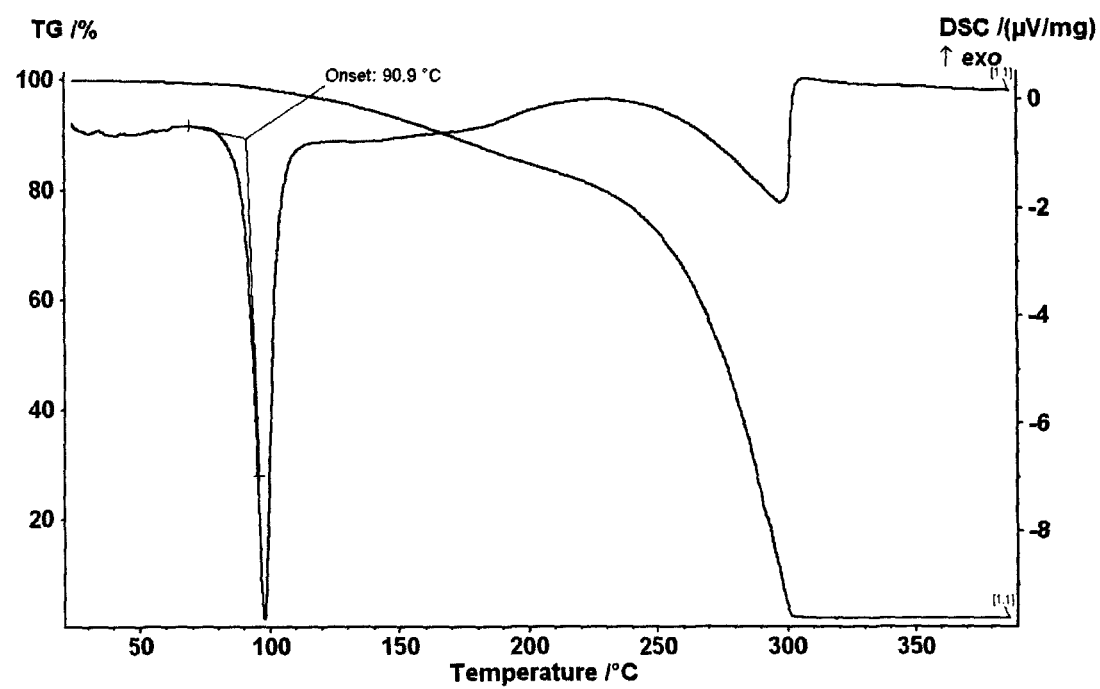
FIG. 2 is a thermogravimetric analysis (TGA) of bis(2,2-dimethyl-5(1-dimethylamino-2-propylimino)-3-hexanonato-N,O,N')strontium 1-Methyl-2-pyrrolidinone adduct.

A plurality of metal-containing complexes of a multidentate ketoiminate, a first embodiment of which is represented by the structure shown below:

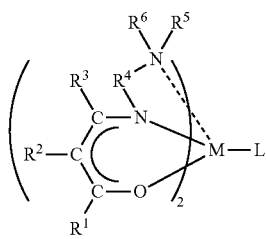

Formula 1 wherein M is a group 2 metals including magnesium, calcium, strontium, barium; wherein $R^1$ is selected from the group consisting of branched alkyl, fluoroalkyl, cycloaliphatic, and aryl, having from 4 to 10 carbon atoms; $R^2$ can be from the group consisting of hydrogen, alkyl, alkoxy, cycloaliphatic, and aryl; $R^3$ is linear or branched selected from the group consisting of alkyl, fluoroalkyl, cycloaliphatic, and aryl; $R^4$ is a linear or branched alkyl bridge having 2 to 10 carbon atoms; $R^{5-6}$ are individually selected from the group consisting of $C_{1-2}$ alkyl; L is a neutral ligand coordinated to the metal via an oxygen or nitrogen atom. Exemplary neutral ligands include, but not limited, ether, amines, polyamine, polyether, organic amides, alcohol, and ketones.

Second embodiment of which is represented by the structure shown below:

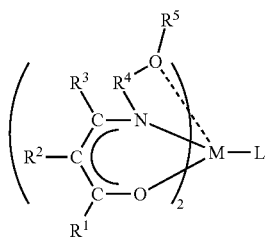

Formula 2 wherein M is a group 2 metals including magnesium, calcium, strontium, barium; wherein $R^1$ is selected from the group consisting of branched alkyl, fluoroalkyl, cycloaliphatic, and aryl, having from 4 to 10 carbon atoms; $R^2$ can be from the group consisting of hydrogen, alkyl, alkoxy, cycloaliphatic, and aryl; $R^3$ is linear or branched selected from the group consisting of alkyl, fluoroalkyl, cycloaliphatic, and aryl; $R^4$ is a liner or branched alkyl bridge having 2 to 10 carbon atoms; $R^5$ is selected from the group consisting of $C_{1-2}$ alkyl; L is a neutral ligand coordinated to the metal via an oxygen or nitrogen atom. Exemplary neutral ligands include, but not limited, ether, amines, polyether, polyamine, organic amides, alcohol, and ketones.

The third embodiment of which is represented by the structure shown below:

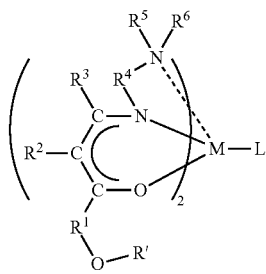

Formula 3 wherein M is a group 2 metals including magnesium, calcium, strontium, barium; wherein $R^1$ is selected from the group consisting of branched alkyl, fluoroalkyl, cycloaliphatic, and aryl, having from 4 to 10 carbon atoms; $R^2$ can be from the group consisting of hydrogen, alkyl, alkoxy, cycloaliphatic, and aryl; $R^3$ is linear or branched selected from the group consisting of alkyl, fluoroalkyl, cycloaliphatic, and aryl; $R^4$ is a liner or branched alkyl bridge having 2 to 10 carbon atoms; $R^{5-6}$ are individually selected from the group consisting of $C_{1-2}$ alkyl, R' is selected from the group consisting of $C_{1-2}$ alkyl; L is a neutral ligand coordinated to the metal via an oxygen or nitrogen atom. Exemplary neutral ligands include, but not limited, ether, amines, polyether, polyamine, organic amides, alcohol, and ketones.

The fourth embodiment of which is represented by the structure shown below:

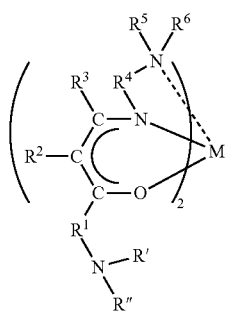

Formula 4 wherein M is a group 2 metals including magnesium, calcium, strontium, barium; wherein $R^1$ is selected from the group consisting of branched alkyl, fluoroalkyl, cycloaliphatic, and aryl, having from 4 to 10 carbon atoms; $R^2$ can be from the group consisting of hydrogen, alkyl, alkoxy, cycloaliphatic, and aryl; $R^3$ is linear or branched selected from the group consisting of alkyl, fluoroalkyl, cycloaliphatic, and aryl; $R^4$ is a liner or branched alkyl bridge having 2 to 10 carbon atoms; $R^{5-6}$ are individually selected from the group consisting of $C_{1-2}$ alkyl, R' and R" are individually selected from the group consisting of $C_{1-2}$ alkyl.

The fifth embodiment of which is represented by the structure shown below:

Formula 5

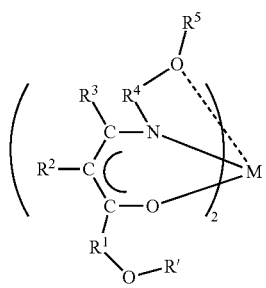

wherein M is a group 2 metals including magnesium, calcium, strontium, barium; wherein $R^1$ is selected from the group consisting of branched alkyl, fluoroalkyl, cycloaliphatic, and aryl, having from 4 to 10 carbon atoms; $R^2$ can be from the group consisting of hydrogen, alkyl, alkoxy, cycloaliphatic, and aryl; $R^3$ is linear or branched selected from the group consisting of alkyl, fluoroalkyl, cycloaliphatic, and aryl; $R^4$ is a liner or branched alkyl bridge having 2 to 10 carbon atoms; $R^5$ is selected from the group consisting of $C_{1-2}$ alkyl, R' is selected from the group consisting of $C_{1-2}$ alkyl.

The sixth embodiment of which is represented by the structure shown below:

Formula 6

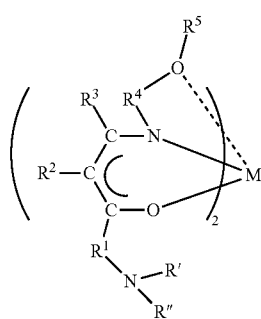

wherein M is a group 2 metals including magnesium, calcium, strontium, barium; wherein $R^1$ is selected from the group consisting of branched alkyl, fluoroalkyl, cycloaliphatic, and aryl, having from 4 to 10 carbon atoms; $R^2$ can be from the group consisting of hydrogen, alkyl, alkoxy, cycloaliphatic, and aryl; $R^3$ is linear or branched selected from the group consisting of alkyl, fluoroalkyl, cycloaliphatic, and aryl; $R^4$ is a liner or branched alkyl bridge having 2 to 10 carbon atoms; $R^5$ is selected from the group consisting of $C_{1-2}$ alkyl, R' and R" are individually selected from the group consisting of $C_{1-2}$ alkyl.

The seventh embodiment of which is represented by the structure shown below:

Formula 7

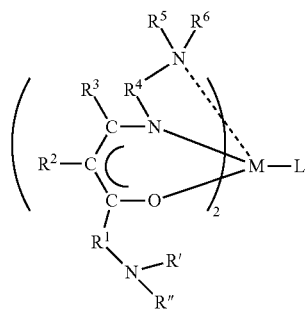

wherein M is a group 2 metals including magnesium, calcium, strontium, barium; wherein $R^1$ is selected from the group consisting of branched alkyl, fluoroalkyl, cycloaliphatic, and aryl, having from 4 to 10 carbon atoms; $R^2$ can be from the group consisting of hydrogen, alkyl, alkoxy, cycloaliphatic, and aryl; $R^3$ is linear or branched selected from the group consisting of alkyl, fluoroalkyl, cycloaliphatic, and aryl; $R^4$ is a liner or branched alkyl bridge having 2 to 10 carbon atoms; $R^{5-6}$ are individually selected from the group consisting of $C_{1-2}$ alkyl, R' and R" are individually selected from the group consisting of $C_{1-2}$ alkyl; L is a neutral ligand coordinated to the metal via an oxygen or nitrogen atom. Exemplary neutral ligands include, but not limited, ether, amines, polyether, polyamine, organic amides, alcohol, and ketones.

The eighth embodiment of which is represented by the structure shown below:

Formula 8

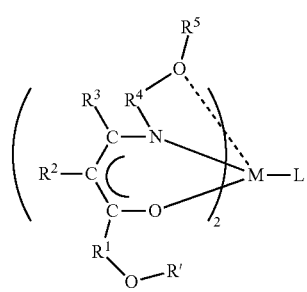

wherein M is a group 2 metals including magnesium, calcium, strontium, barium; wherein $R^1$ is selected from the group consisting of branched alkyl, fluoroalkyl, cycloaliphatic, and aryl, having from 4 to 10 carbon atoms; $R^2$ can be from the group consisting of hydrogen, alkyl, alkoxy, cycloaliphatic, and aryl; $R^3$ is linear or branched selected from the group consisting of alkyl, fluoroalkyl, cycloaliphatic, and aryl; $R^4$ is a liner or branched alkyl bridge having 2 to 10 carbon atoms; $R^5$ are individually selected from the group consisting of $C_{1-2}$ alkyl, R' is selected from the group consisting of $C_{1-2}$ alkyl; L is a neutral ligand coordinated to the metal via an oxygen or nitrogen atom. Exemplary neutral ligands include, but not limited, ether, amines, polyether, polyamine, organic amides, alcohol, and ketones.

The ninth embodiment of which is represented by the structure shown below:

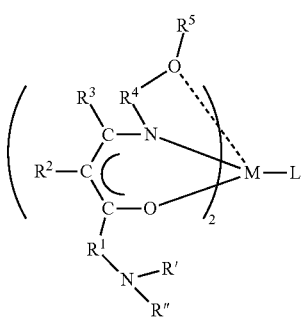

Formula 9 wherein M is a group 2 metals including magnesium, calcium, strontium, barium; wherein $R^1$ is selected from the group consisting of branched alkyl, fluoroalkyl, cycloaliphatic, and aryl, having from 4 to 10 carbon atoms; $R^2$ can be from the group consisting of hydrogen, alkyl, alkoxy, cycloaliphatic, and aryl; $R^3$ is linear or branched selected from the group consisting of alkyl, fluoroalkyl, cycloaliphatic, and aryl; $R^4$ is a liner or branched alkyl bridge having 2 to 10 carbon atoms; $R^5$ is selected from the group consisting of $C_{1-2}$ alkyl, R' and R" are individually selected from the group consisting of $C_{1-2}$ alkyl; L is a neutral ligand coordinated to the metal via an oxygen or nitrogen atom. Exemplary neutral ligands include, but not limited, ether, amines, polyether, polyamine, organic amides, alcohol, and ketones.

The present invention is also a metal containing complex, as described variously above, dissolved in a solvent selected from the group consisting of glyme solvents having from 1 to 20 ethoxy —($C_2H_4O$)— repeat units; $C_2$-$C_{12}$ alkanols, organic ethers selected from the group consisting of dialkyl ethers comprising $C_1$-$C_6$ alkyl moieties, $C_4$-$C_8$ cyclic ethers; $C_{12}$-$C_{60}$ crown $O_4$-$O_{20}$ ethers wherein the prefixed $C_i$ range is the number i of carbon atoms in the ether compound and the suffixed $O_j$ range is the number i of oxygen atoms in the ether compound; $C_6$-$C_{12}$ aliphatic hydrocarbons; $C_6$-$C_{18}$ aromatic hydrocarbons; organic esters; organic amines; polyamines and organic amides.

In one embodiment, the solvent is same as the neutral ligand coordinated to the metal.

Another embodiment is a vapor deposition process for forming a conformal metal oxide thin film on a substrate wherein a precursor source and an oxygen containing agent are introduced to a deposition chamber and a metal oxide film deposited on a substrate, the improvement which comprises using the metal complex of claim 1 as said precursor source.

A further embodiment is a vapor deposition process for forming a conformal metal oxide thin film on a substrate wherein a precursor source and an oxygen containing agent are introduced to a deposition chamber and a metal oxide film deposited on a substrate, the improvement which comprises using the metal complex, as variously described above, as said precursor source.

EXAMPLES

Example 1

Synthesis of bis(2,2-dimethyl-5(1-dimethylamino-2-propylimino)-3-hexanonato-N,O,N')strontium THF adduct 100 g (185.76 mmol) of bis(2,2-dimethyl-5(1-dimethylamino-2-propylimino)-3-hexanonato-N,O,N')strontium was heated as a homogenous solution in 400 mL of tetrahydrofuran (THF). As the solution cooled to room temperature, clear crystals began to form. After several hours of letting the crystals grow undisturbed, the mother solution was decanted off. The crystals were washed with cold hexane and dried under vacuum. Upon subjecting the crystals to vacuum, they began to crack and pop indicating that solvent was either trapped in the crystal lattice or had bonded directly to the strontium.

Elemental analysis: calcd for $C_{30}H_{68}N_4O_3Sr$: C, 59.03; N, 9.18; H, 9.58. Found: C, 55.03; N, 9.41; H, 9.62. $^1H$ NMR (500 MHz, $C_6D_6$): δ=5.12 (s, 2H), 3.59 (t, 4H), 3.43 (m, 2H), 1.90 (b, 12H), 1.83 (s, 6H), 1.75 (m, 4H), 1.42 (s, 18H), 0.96 (d, 6H).

TGA analysis confirmed the existence of THF in the crystals and showed according to the mass loss that approximately one THF had coordinated to every one strontium beta-ketoiminate. Aside from release of THF, the melting point of the crystals was nearly identical to the strontium beta-ketoiminate alone. X-ray single crystal structure analysis confirmed that one THF had directly coordinated to the strontium to make a seven coordinated metal complex.

Example 2

Synthesis of bis(2,2-dimethyl-5-(dimethylaminoethyl-imino)-3-hexanonato-N,O,N')strontium THF adduct 1.00 g (1.96 mmol) of bis(2,2-dimethyl-5-(dimethylaminoethyl-imino)-3-hexanonato-N,O,N')strontium was heated into 5 mL of THF. The homogenous solution was then filtered through a 0.45 µm syringe filter and left to slowly evaporate at room temperature. Clear crystals formed as a result.

Elemental analysis: calcd for $C_{28}H_{54}N_4O_3Sr$: C, 57.75; N, 9.62; H, 9.35. Found: C, 53.03; N, 9.91; H, 9.51. $^1H$ NMR (500 MHz, $C_6D_6$): δ=5.17 (s, 2H), 3.58 (t, 4H), 2.98 (t, 4H), 2.28 (b, 4H), 1.91 (s, 12H), 1.78 (s, 6H), 1.43 (t, 4H), 1.39 (s, 18H).

TGA analysis confirmed the existence of THF in the crystals and showed according to the mass loss that approximately one THF had coordinated to every one strontium beta-ketoiminate. Aside from release of THF, the melting point of the crystals was nearly identical to the strontium beta-ketoiminate alone. X-ray analysis confirmed that one THF had directly coordinated to the metal center to make a seven coordinated strontium complexes.

Example 3

Synthesis of bis(2,2-dimethyl-5(1-dimethylamino-2-propylimino)-3-hexanonato-N,O,N')strontium 1-Methyl-2-pyrrolidinone(NMP) adduct To a suspension of 1.00 g (1.86 mmol) of bis(2,2-dimethyl-5(1-dimethylamino-2-propylimino)-3-hexanonato-N,O,N') strontium in 5 mL of hexanes was added 0.18 g (1.86 mmol) of 1-Methyl-2-pyrrolidinone. Resulting solution was left to slowly evaporate at room temperature. Resulting solid was heated into 3 mL of hexanes and then filtered through a 0.45 µm syringe filter and left to recrystallize. Clear crystals formed as a result. The yield was 67% on the basis of strontium.

Elemental analysis: calcd for $C_{31}H_{59}N_5O_3Sr$: C, 58.41; N, 10.99; H, 9.33. Found: C, 57.30; N, 10.93; H, 10.10. $^1H$ NMR (500 MHz, $C_6D_6$): δ=5.11 (s, 2H), 3.46 (m, 2H), 2.46 (s, 3H), 2.44 (t, 2H), 1.98 (t, 2H), 1.87 (s, 12H), 1.84 (s, 6H), 1.77 (m, 4H), 1.41 (s, 18H), 1.18 (q, 2H), 0.98 (d, 6H).

X-ray single crystal structure analysis (FIG. 1) confirmed that one NMP had directly coordinated to the strontium to make a seven coordinated metal complex. TGA analysis indicates the complex has much lower melting point than that without adduct, i.e. 91° C. vs 163° C. for bis(2,2-dimethyl-5 (1-dimethylamino-2-propylimino)-3-hexanonato-N,O,N') strontium.

Example 4

Synthesis of bis(2,2-dimethyl-5-(dimethylaminoethyl-imino)-3-hexanonato-N,O,N')strontium 1-Methyl-2-pyrrolidinone(NMP) adduct To a suspension of 1.00 g (1.96 mmol) of bis(2,2-dimethyl-5-(dimethylaminoethyl-imino)-3-hexanonato-N,O,N')strontium in 5 mL of hexanes was added 0.19 g (1.96 mmol) of 1-Methyl-2-pyrrolidinone. The resulting solution was left to slowly evaporate at room temperature. A solid formed and was heated into 3 mL of hexanes and then filtered through a 0.45 μm syringe filter and left to recrystallize. Clear crystals formed.

Elemental analysis: calcd for $C_{26}H_{55}N_5O_3Sr$: C, 57.16; N, 11.49; H, 9.10. Found: C, 54.84; N, 11.29; H, 8.78. $^1$H NMR (500 MHz, $C_6D_6$): δ=5.16 (s, 2H), 3.05 (t, 4H), 2.46 (t, 2H), 2.46 (s, 3H), 2.35 (t, 4H), 1.99 (t, 2H), 1.99 (s, 12H), 1.80 (s, 6H), 1.40 (s, 18H), 1.20 (q, 2H).

X-ray single crystal structure analysis confirmed that one NMP had directly coordinated to the strontium to make a seven coordinated metal complex. TGA analysis indicates the complex has much lower melting point than that without adduct, i.e. 83° C. vs 190° C. for bis(2,2-dimethyl-5-(dimethylaminoethyl-imino)-3-hexanonato-N,O,N')strontium.

Example 5

Synthesis of bis(2,2-dimethyl-5(1-dimethylamino-2-propylimino)-3-hexanonato-N,O,N')strontium pyridine adduct To a solution of 1.00 g (1.86 mmol) bis(2,2-dimethyl-5(1-dimethylamino-2-propylimino)-3-hexanonato-N,O,N') strontium in 5 mL of hexanes was added 0.15 g (1.86 mmol) of pyridine. Upon addition, a white precipitate was formed. The mixture was stirred for several hours after which hexanes were removed under vacuum. Obtained a white solid weighing 1.10 g. Crystals were grown from heating solid into octane.

$^1$H NMR (500 MHz, $C_6D_6$): δ=8.63 (m, 2H), 6.96 (m, 1H), 6.69 (m, 2H), 5.14 (s, 2H), 3.51 (t, 2H), 3.47 (m, 2H), 1.91 (b, 12H), 1.86 (s, 6H), 1.78 (dd, 2H), 1.39 (s, 18H), 0.97 (d, 6H).

X-ray single crystal structure analysis confirmed that one pyridine had directly coordinated to the strontium to make a seven coordinated metal complex.

Example 6

Synthesis of bis(2,2-dimethyl-5(1-dimethylamino-2-propylimino)-3-hexanonato-N,O,N')strontium 1-Cyclohexyl-2-pyrrolidone adduct To a solution of 1.00 g (1.86 mmol) of bis(2,2-dimethyl-5 (1-dimethylamino-2-propylimino)-3-hexanonato-N,O,N') strontium in 5 mL of hexanes was added 0.31 g (1.86 mmol) of 1-Cyclohexyl-2-pyrrolidone. Resulting solution was left to slowly evaporate at room temperature yielding a waxy solid. TGA indicates a melting point at 97° C.

Example 7

Synthesis of bis(2,2-dimethyl-5(1-dimethylamino-2-propylimino)-3-hexanonato-N,O,N')strontium N,N-Diethylacetamide adduct To a solution of 1.00 g (1.86 mmol) of bis(2,2-dimethyl-5 (1-dimethylamino-2-propylimino)-3-hexanonato-N,O,N') strontium in 5 mL of hexanes was added 0.21 g (1.86 mmol) of N,N-Diethylacetamide. Resulting solution was left to slowly evaporate at room temperature yielding crystals. TGA indicates a melting point at 102° C.

X-ray single crystal structure analysis confirmed that one N,N-Diethylacetamide had directly coordinated to the strontium to make a seven coordinated metal complex.

Elemental analysis: calcd for $C_{32}H_{63}N_5O_3Sr$: C, 58.81; N, 10.72; H, 9.72. Found: C, 57.28; N, 10.52; H, 9.58.

The invention claimed is:

1. A compound having the formula:

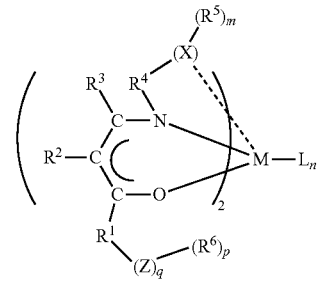

wherein M is selected from the group consisting of magnesium, calcium, strontium, barium; wherein $R^1$ is selected from the group consisting of branched alkyl, fluoroalkyl, cycloaliphatic, a $C_6$ aryl and a $C_{10}$ aryl; $R^2$ is selected from the group consisting of hydrogen, alkyl, alkoxy, cycloaliphatic, and aryl; $R^3$ is linear or branched selected from the group consisting of alkyl, fluoroalkyl, cycloaliphatic, and aryl; $R^4$ is a linear or branched alkyl bridge having 2 to 10 carbon atoms; $R^{5-6}$ are individually selected from the group consisting of $C_{1-2}$ alkyl; L is a neutral ligand coordinated to the metal via an oxygen or nitrogen atom; n is 0 or 1; X and Z are independently selected from O or N; when X is N, m is 2 and the two $R^5$ are each independently selected from the group consisting of $C_{1-2}$ alkyl; when X is O, m is 1 and $R^5$ is selected from the group consisting of $C_{1-2}$ alkyl; q can be 0 or 1; when q is 0, Z and $R^6$ are not present; when q is 1, Z is either N, p is 2 and the two $R^6$ are each independently selected from the group consisting of $C_{1-2}$ alkyl; or Z is O, p is 1 and $R^6$ is selected from the group consisting of $C_{1-2}$ alkyl; when q is 0, n must be 1; when X is N and Z is O and q is 1, n must be 1.

2. The compound of claim 1 having the formula:

Formula 1

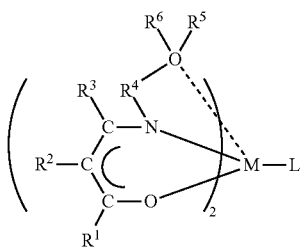

wherein M is selected from the group consisting of magnesium, calcium, strontium, and barium; wherein $R^1$ is selected from the group consisting of branched alkyl, fluoroalkyl, cycloaliphatic, a $C_6$ aryl and a $C_{10}$ aryl; $R^2$ is selected from the group consisting of hydrogen, alkyl, alkoxy, cycloaliphatic, and aryl; $R^3$ is linear or branched selected from the group consisting of alkyl, fluoroalkyl, cycloaliphatic, and aryl; $R^4$ is a linear or branched alkyl bridge having 2 to 10 carbon atoms; $R^{5-6}$ are individually selected from the group consisting of $C_{1-2}$ alkyl; L is a neutral ligand coordinated to the metal via an oxygen or nitrogen atom.

3. The compound of claim 1 having the formula:

Formula 2

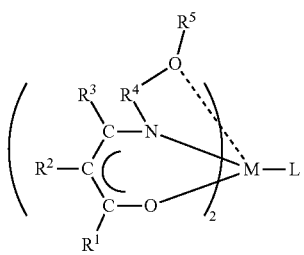

wherein M is selected from the group consisting of magnesium, calcium, strontium, and barium; wherein $R^1$ is selected from the group consisting of branched alkyl, fluoroalkyl, cycloaliphatic, and a $C_6$ aryl and a $C_{10}$ aryl; $R^2$ is selected from the group consisting of hydrogen, alkyl, alkoxy, cycloaliphatic, and aryl; $R^3$ is linear or branched selected from the group consisting of alkyl, fluoroalkyl, cycloaliphatic, and aryl; $R^4$ is a linear or branched alkyl bridge having 2 to 10 carbon atoms; $R^5$ is selected from the group consisting of $C_{1-2}$ alkyl; L is a neutral ligand coordinated to the metal via an oxygen or nitrogen atom.

4. The compound of claim 1 having the formula:

Formula 3

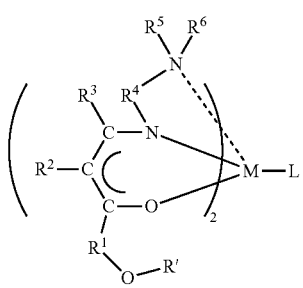

wherein M is selected from the group consisting of magnesium, calcium, strontium, and barium; wherein $R^1$ is selected from the group consisting of branched alkyl, fluoroalkyl, cycloaliphatic, and a $C_6$ aryl and a $C_{10}$ aryl; $R^2$ is selected from the group consisting of hydrogen, alkyl, alkoxy, cycloaliphatic, and aryl; $R^3$ is linear or branched selected from the group consisting of alkyl, fluoroalkyl, cycloaliphatic, and aryl; $R^4$ is a linear or branched alkyl bridge having 2 to 10 carbon atoms; $R^{5-6}$ are individually selected from the group consisting of $C_{1-2}$ alkyl, R is selected from the group consisting of $C_{1-2}$ alkyl; L is a neutral ligand coordinated to the metal via an oxygen or nitrogen atom.

5. The compound of claim 1 having the formula:

Formula 4

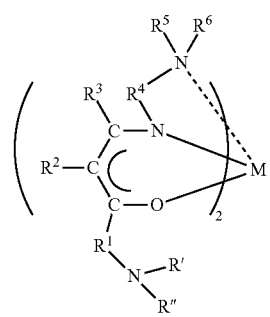

wherein M is selected from the group consisting of magnesium, calcium, strontium, and barium; wherein $R^1$ is selected from the group consisting of branched alkyl, fluoroalkyl, cycloaliphatic, and a $C_6$ aryl and a $C_{10}$ aryl; $R^2$ is selected from the group consisting of hydrogen, alkyl, alkoxy, cycloaliphatic, and aryl; $R^3$ is linear or branched selected from the group consisting of alkyl, fluoroalkyl, cycloaliphatic, and aryl; $R^4$ is a linear or branched alkyl bridge having 2 to 10 carbon atoms; $R^{5-6}$ are individually selected from the group consisting of $C_{1-2}$ alkyl, R and R are individually selected from the group consisting of $C_{1-2}$ alkyl.

6. The compound of claim 1 having the formula:

Formula 5

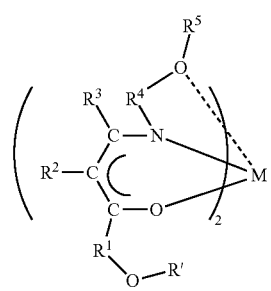

wherein M is selected from the group consisting of magnesium, calcium, strontium, and barium; wherein $R^1$ is selected from the group consisting of branched alkyl, fluoroalkyl, cycloaliphatic, and a $C_6$ aryl and a $C_{10}$ aryl; $R^2$ is selected from the group consisting of hydrogen, alkyl, alkoxy, cycloaliphatic, and aryl; $R^3$ is linear or branched selected from the group consisting of alkyl, fluoroalkyl, cycloaliphatic, and aryl; $R^4$ is a linear or branched alkyl bridge having 2 to 10 carbon atoms; $R^5$ is selected from the group consisting of $C_{1-2}$ alkyl, R is selected from the group consisting of $C_{1-2}$ alkyl.

7. The compound of claim 1 having the formula:

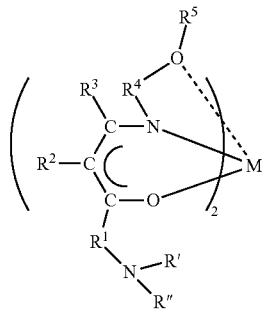

Formula 6 wherein M is selected from the group consisting of magnesium, calcium, strontium, and barium; wherein $R^1$ is selected from the group consisting of branched alkyl, fluoroalkyl, cycloaliphatic, and a $C_6$ aryl and a $C_{10}$ aryl; $R^2$ is selected from the group consisting of hydrogen, alkyl, alkoxy, cycloaliphatic, and aryl; $R^3$ is linear or branched selected from the group consisting of alkyl, fluoroalkyl, cycloaliphatic, and aryl; $R^4$ is a linear or branched alkyl bridge having 2 to 10 carbon atoms; $R^5$ is selected from the group consisting of $C_{1-2}$ alkyl, R and R are individually selected from the group consisting of $C_{1-2}$ alkyl.

8. The compound of claim 1 having the formula:

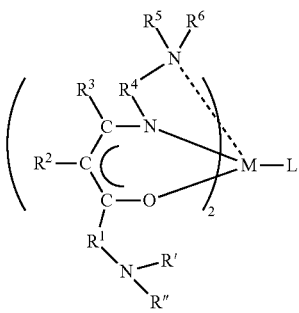

Formula 7 wherein M is selected from the group consisting of magnesium, calcium, strontium, and barium; wherein $R^1$ is selected from the group consisting of branched alkyl, fluoroalkyl, cycloaliphatic, and a $C_6$ aryl and a $C_{10}$ aryl; $R^2$ is selected from the group consisting of hydrogen, alkyl, alkoxy, cycloaliphatic, and aryl; $R^3$ is linear or branched selected from the group consisting of alkyl, fluoroalkyl, cycloaliphatic, and aryl; $R^4$ is a linear or branched alkyl bridge having 2 to 10 carbon atoms; $R^{5-6}$ are individually selected from the group consisting of $C_{1-2}$ alkyl, R and R are individually selected from the group consisting of $C_{1-2}$ alkyl; L is a neutral ligand coordinated to the metal via an oxygen or nitrogen atom.

9. The compound of claim 1 having the formula:

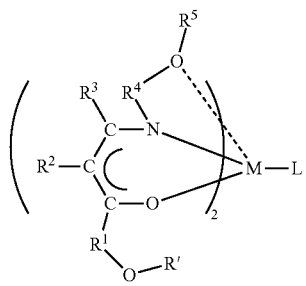

Formula 8 wherein M is selected from the group consisting of magnesium, calcium, strontium, and barium; wherein $R^1$ is selected from the group consisting of branched alkyl, fluoroalkyl, cycloaliphatic, and a $C_6$ aryl and a $C_{10}$ aryl; $R^2$ is selected from the group consisting of hydrogen, alkyl, alkoxy, cycloaliphatic, and aryl; $R^3$ is linear or branched selected from the group consisting of alkyl, fluoroalkyl, cycloaliphatic, and aryl; $R^4$ is a linear or branched alkyl bridge having 2 to 10 carbon atoms; $R^5$ is selected from the group consisting of $C_{1-2}$ alkyl, R is selected from the group consisting of $C_{1-2}$ alkyl; L is a neutral ligand coordinated to the metal via an oxygen or nitrogen atom.

10. The compound of claim 1 having the formula:

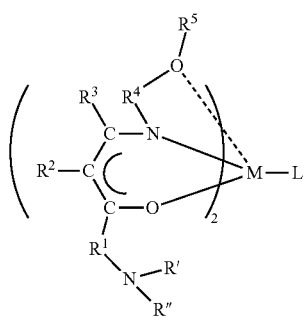

Formula 9 wherein M is selected from the group consisting of magnesium, calcium, strontium, and barium; wherein $R^1$ is selected from the group consisting of branched alkyl, fluoroalkyl, cycloaliphatic, and a $C_6$ aryl and a $C_{10}$ aryl; $R^2$ is selected from the group consisting of hydrogen, alkyl, alkoxy, cycloaliphatic, and aryl; $R^3$ is linear or branched selected from the group consisting of alkyl, fluoroalkyl, cycloaliphatic, and aryl; $R^4$ is a linear or branched alkyl bridge having 2 to 10 carbon atoms; $R^5$ is selected from the group consisting of $C_{1-2}$ alkyl, R and R are individually selected from the group consisting of $C_{1-2}$ alkyl; L is a neutral ligand coordinated to the metal via an oxygen or nitrogen atom.

11. The compound of claim 1 wherein the neutral ligand is selected from the group consisting of ether, amines, organic amides, and ketones.

12. A composition comprising the compound of claim 1 dissolved in a solvent selected from the group consisting of glyme solvents having from 1 to 20 ethoxy —$(C_2H_4O)$— repeat units; $C_2$-$C_{12}$ alkanols, organic ethers selected from the group consisting of dialkyl ethers comprising $C_1$-$C_6$ alkyl moieties, $C_4$-$C_8$ cyclic ethers; $C_{12}$-$C_{60}$ crown $O_4$-$O_{20}$ ethers wherein the prefixed $C_i$ range is the number i of carbon atoms in the ether compound and the suffixed $O_i$ range is the number i of oxygen atoms in the ether compound; $C_6$-$C_{12}$ aliphatic hydrocarbons; $C_6$-$C_{18}$ aromatic hydrocarbons; organic esters; organic amines; polyamines and organic amides.

13. A vapor deposition process for forming a conformal metal oxide thin film on a substrate, wherein the metal is selected from the group consisting of magnesium, calcium, strontium and barium the process comprising: introducing a precursor source and an oxygen containing agent into a deposition chamber to deposit the metal oxide film on the substrate, the improvement which comprises using the compound of claim 1 as said precursor source.

14. A vapor deposition process for forming a conformal metal oxide thin film on a substrate, wherein the metal is selected from the group consisting of magnesium, calcium, strontium and barium the process comprising: introducing a precursor source and an oxygen containing agent into a deposition chamber to deposit the metal oxide film on the substrate, the improvement which comprises using the composition of claim 12 as said precursor source.

* * * * *

UNITED STATES PATENT AND TRADEMARK OFFICE
CERTIFICATE OF CORRECTION

PATENT NO.        : 9,079,923 B2                              Page 1 of 1
APPLICATION NO.   : 13/187833
DATED             : July 14, 2015
INVENTOR(S)       : Xinjian Lei and Daniel P. Spence It is certified that error appears in the above-identified patent and that said Letters Patent is hereby corrected as shown below:

In the claims,

Column 12, Line 41
In claim 5 delete words "R and R" and insert words -- R' and R" --

Column 13, Line 30
In claim 7 delete words "R and R" and insert words -- R' and R" --

Column 13, Line 62
In claim 8 delete words "R and R" and insert words -- R' and R" --

Column 14, Line 24
In claim 9 delete words "R is" and insert words -- R' is --

Column 14, Line 54
In claim 10 delete words "R and R" and insert words -- R' and R" --

Signed and Sealed this
Seventeenth Day of May, 2016

Michelle K. Lee
*Director of the United States Patent and Trademark Office*